(12) United States Patent
Quint

(10) Patent No.: US 7,972,324 B2
(45) Date of Patent: Jul. 5, 2011

(54) CATHETER AND METHOD OF MANUFACTURING SAME

(75) Inventor: Bodo Quint, Rottenburg-Seebronn (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 1417 days.

(21) Appl. No.: 10/744,064

(22) Filed: Dec. 24, 2003

(65) Prior Publication Data

US 2004/0210210 A1    Oct. 21, 2004

(30) Foreign Application Priority Data

Dec. 31, 2002    (EP) .................................... 02029115

(51) Int. Cl.
*A61M 25/00*    (2006.01)

(52) U.S. Cl. ..................................... 604/525; 604/96.01

(58) Field of Classification Search .......... 604/523–527, 604/101.01, 101.02, 96.01, 103
See application file for complete search history.

(56) References Cited

U.S. PATENT DOCUMENTS

| | | | |
|---|---|---|---|
| 3,173,418 A * | 3/1965 | Baran | 128/207.15 |
| 3,938,502 A | 2/1976 | Bom | |
| 4,648,384 A * | 3/1987 | Schmukler | 600/18 |
| 4,782,834 A | 11/1988 | Maguire et al. | |
| 5,171,232 A | 12/1992 | Castillo et al. | |
| 5,242,394 A | 9/1993 | Tremulis | |
| 5,504,121 A | 4/1996 | West | |
| 5,554,121 A | 9/1996 | Ainsworth et al. | |
| 5,700,252 A * | 12/1997 | Klingenstein | 604/525 |
| 5,746,701 A | 5/1998 | Noone | |
| 5,971,975 A | 10/1999 | Mills et al. | |
| 6,017,323 A * | 1/2000 | Chee | 604/96.01 |
| 6,569,148 B2 | 5/2003 | Bagaoisan et al. | |
| 2002/0156459 A1 * | 10/2002 | Ye et al. | 604/527 |

FOREIGN PATENT DOCUMENTS

| | | |
|---|---|---|
| EP | 0334640 | 9/1989 |
| JP | 02-232065 | 9/1990 |
| JP | 05-011996 | 2/1993 |
| JP | 10-263088 | 10/1998 |
| JP | 11-114068 | 4/1999 |
| JP | 2000-185103 | 7/2000 |
| WO | WO 95/29726 | 11/1995 |
| WO | WO 00/76404 | 12/2000 |

* cited by examiner

*Primary Examiner* — Nicholas D Lucchesi
*Assistant Examiner* — Theodore J Stigell
(74) *Attorney, Agent, or Firm* — Workman Nydegger

(57) ABSTRACT

A catheter basically has a catheter shaft in which a catheter tip of which is provided with a joint made of a material which is more flexible than the material of the catheter shaft. The joint is disposed between the distal end of the catheter shaft and the distal end of the catheter tip. The front end consists of a material being the same or more rigid than that of the catheter shaft.

15 Claims, 1 Drawing Sheet

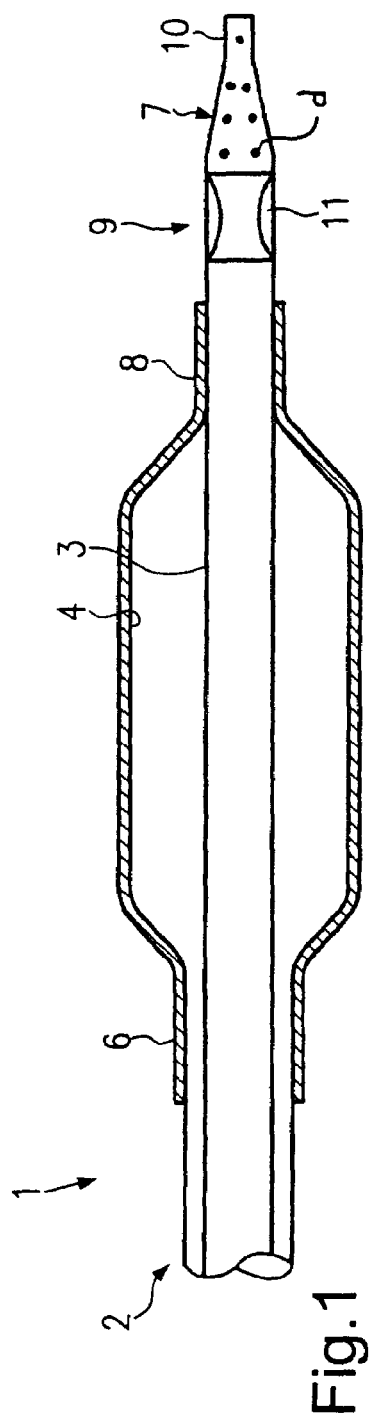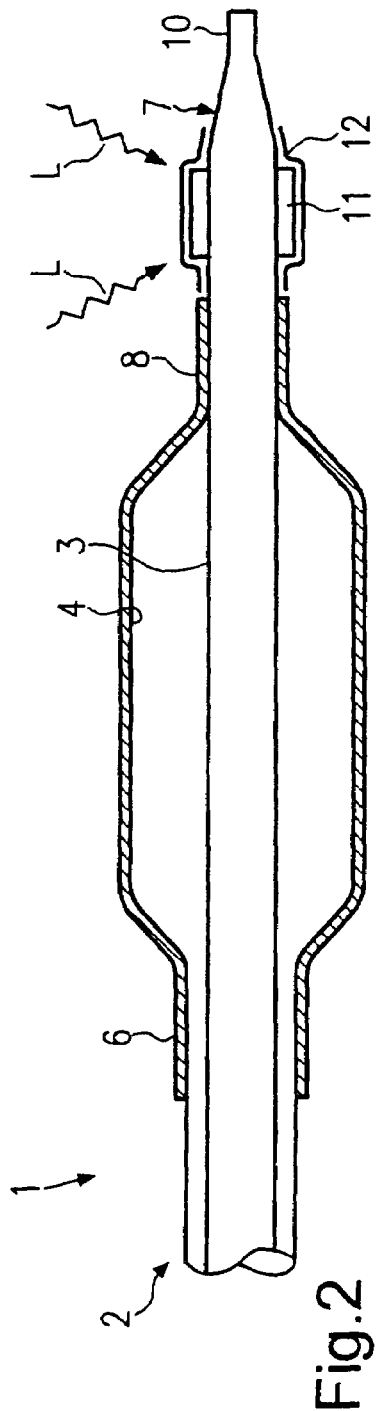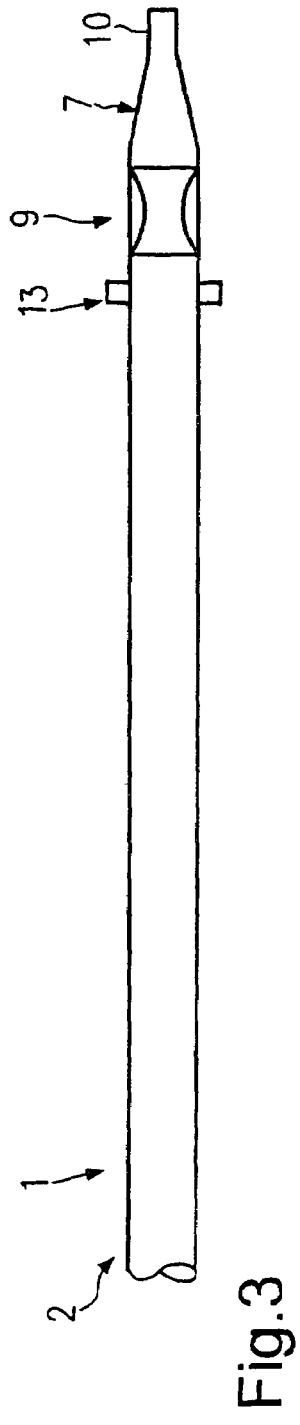

CATHETER AND METHOD OF MANUFACTURING SAME

BACKGROUND OF THE INVENTION

1. Field of the Invention

The present invention generally relates to a catheter as well as a method for producing same.

2. Background Information

For an expansion of a stenosis in body vessels or body hollows, catheter arrangements are used nowadays which comprise an expandable balloon at their distal ends. A stent may additionally be crimped on the expandable balloon, which can be placed in the stenosis for stabilizing the vascular wall. The catheter arrangement is guided to the constricted position in the patient's body with the help of a guiding wire. The stenosis is then expanded by expanding the balloon or the crimped stent is placed in the stenosis, respectively.

A catheter having a soft tip is disclosed in U.S. Pat. No. 4,782,834. However, the soft tip of this catheter is achieved by a material transition to a material of lesser stability. This means that the complete tip is made of the soft material, resulting in the problem that this portion tends to bend. A possible result thereof is a deformation of the tip, which may lead to a constriction of the inner lumen or a permanent deformation.

The quality of a balloon catheter stands out due to the fact that the catheter can follow winding vessels easily and that the catheter can be pushed as far as possible into a stenosis, guided by the guide wire ("tracking"). This tracking is supported by the fact that the tip is flexible enough to guide the balloon. In case when in particular the distal end, also referred to as tip, is made from an especially suitable flexible material, the complete system follows the windings of the vessel. At the same time, it has to be guaranteed that the catheter can be securely pushed into the constricted portions of the vessel. This property is referred to as "pushability". In case the complete catheter tip, as that of the U.S. Pat. No. 4,782,834, is formed of a soft material, in particular this required property is negatively affected. When pushing the catheter tip, same can be deformed reversibly or irreversibly and therefore also an entangling at the guide wire can occur (friction). With decreasing size of the profile of the tip, i.e., the smaller the so-called leasion entry profile, the more the mechanical sensitiveness of the tip increases and the more are the properties of the tip negatively affected by the soft material.

However, as it is desired to have an entry profile of the catheter as small as possible in order to penetrate narrow stenoses, it would be ideal to be able to form a tip having a minimum entry profile but being mechanically stable, featuring a continuously increasing diameter, but being flexible and having a homogenous transition into the balloon cone.

In view of the above, it will be apparent to those skilled in the art from this disclosure that there exists a need for an improved catheter. This invention addresses this need in the art as well as other needs, which will become apparent to those skilled in the art from this disclosure.

SUMMARY OF THE INVENTION

It is an object of the present invention to provide a catheter having an especially high flexibility at its distal end portion, but also a sufficient stability for achieving a good pushability.

The present invention discloses a catheter and a method for manufacturing same, which provides improved mechanical properties of the tip portion. Preferably, the catheter of the present invention has an entry profile of the catheter as small as possible in order to penetrate narrow stenoses. Moreover, the catheter of the present invention preferably has a tip portion with a minimum entry profile but that is mechanically stable, and featuring a continuously increasing diameter, but being flexible and having a homogenous transition into the balloon cone.

According to the invention, a catheter is provided, the tip of which comprises a joint portion made of a material which is more flexible than the material of the catheter shaft portion. The joint portion is arranged in balloon catheters between the distal end of the balloon and the distal end of the catheter tip portion. In an advantageous embodiment, the distal end of the catheter tip portion is made of the same material as the catheter shaft portion. In a further advantageous embodiment, the distal end of the catheter tip portion is made of a stiffer material than the catheter shaft portion. The catheter tip portion may be for example a metal tip, a metal ring or be made of PTFE, it may be coated, galvanized or X-ray visible or radioopaque. This embodiment can be achieved in a variety of different ways. For example, the tip portion is a one-piece, unitary construction with the shaft portion such that the tip material is the same as the shaft material with the higher stiffness being the result of a treatment process such as the incorporation of additives or particles of a material causing the higher stiffness in the tip portion than the shaft portion. Alternatively, the tip portion is a two piece construction with the tip portion being made of a different material with the higher stiffness and then fixed to the joint portion.

The above arrangement guarantees a nearly optimum combination of flexible tip and high pushability.

In accordance with another aspect of the present invention, a method for manufacturing the inventive catheter as explained above is disclosed. According to an embodiment of this method, a material, e.g., in the form of a metal or plastic ring, is at first applied on a portion between the distal end of the balloon and the front end of the catheter shaft, the material being more flexible than that of the catheter shaft. For prefixing, this ring can be fixed on the catheter shaft by means of a shrinkdown tubing. Subsequently, a welding is carried out by heating with a suitable radiation energy, e.g., monochrome or polychrome light, laser light, electromagnetic radiation, hot air or heat, which integrates the softer material of the ring at the desired position into the catheter shaft by the occurring material flux or material crowding. The welding is preferably executed rotationally symmetrically by a fast and aggressive energy influence. After this integration, the shrinkdown tubing is removed and the joint being movable in all directions is fixed at the desired position in the catheter shaft in its distal tip portion.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure:

FIG. 1 is a schematically simplified longitudinal cross sectional view of a catheter in accordance with a first embodiment of the present invention;

FIG. 2 is an illustration corresponding to FIG. 1 of the distal end portion of the catheter of FIG. 1 for explaining the inventive method in accordance with the present invention; and FIG. 3 is a schematically simplified longitudinal cross sectional view of a catheter corresponding to FIG. 1 of in accordance with a second embodiment of the present invention.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Referring initially to FIG. 1, a distal end of a catheter 1 is illustrated in accordance with a preferred embodiment of the present invention. The catheter 1 basically comprises a customarily formed catheter shaft portion 2 with its distal end 3 having a balloon 4 formed thereon in a conventional manner. The balloon 4 has a proximal end 6 and a distal end 8 arranged on the catheter shaft portion 2.

The catheter shaft portion 2 has a catheter tip portion 7 being part of the catheter shaft portion 2 and protruding beyond the distal end 8 of the balloon 3. The catheter tip portion 7 is for example a metal tip, a metal ring or be made of PTFE. The catheter tip portion 7 can also be coated, galvanized or X-ray visible or radioopaque. In one preferred embodiment, the catheter tip portion 7 is made of the same material as the catheter shaft portion 2. More preferably, the catheter tip portion 7 and the catheter shaft portion 2 are formed together as a one-piece, unitary member. In any event, the catheter tip portion 7 is formed of either a material having the same flexibility and hardness as the material of the catheter shaft portion 2, or a material having less flexibility, i.e., more rigidity, and harder than the catheter shaft portion 2. This construction is illustrated in FIG. 1 by dots d that symbolizes additives or particles that are selectively incorporated into the material of the tip portion 7 such that the catheter tip portion 7 has a higher stiffness than the stiffness of the catheter shaft portion 2. Thus, the catheter tip portion 7 is a one-piece, unitary construction with the catheter shaft portion 2 such that the tip material is the same as the shaft material with the higher stiffness being the result of a treatment process such as the incorporation of additives or particles of a material causing the higher stiffness in the tip portion than the catheter shaft portion. Alternatively, the catheter tip portion 7 is a two piece construction with the catheter tip portion 7 being made of a different material with the higher stiffness and then fixed to a distal end of the joint portion 9.

The catheter tip portion 7 of the inventive catheter 1 comprises a joint portion 9 composed of a material which is more flexible that the material of the catheter shaft portion 2. Preferably, the joint portion 9 is partially constructed of a reduced section of the catheter shaft portion 2 with a material 11 overlying the reduced section of the catheter shaft portion 2 to create an area of greater flexibility than either the catheter tip portion 7 or the catheter shaft portion 2. Thus, the joint portion 9 is more flexible than the material of the catheter shaft portion 2 and the catheter tip portion 7. Thus, a catheter shaft is formed in a plurality of portions of different stiffness to provide optimum strength and flexibility at a point along the length of the catheter shaft that is near the catheter tip portion 7. The joint portion 9 is disposed between the distal end 8 of the balloon 4 and the front end 10 of the catheter tip portion 7 or the catheter shaft portion 2, respectively. As a consequence, a flexible property of the catheter tip portion 7 is achieved on the one hand, whereas on the other hand a high pushability is guaranteed, as the front end 10 of the catheter tip 7 is made of the same rigid material as the catheter shaft 2 or a more rigid material.

In FIG. 2, the distal end portion of the catheter 1 is shown to explain the inventive method. In this method, the catheter shaft portion 2 and the catheter tip portion 7 are formed of a one-piece, unitary member. The joint portion 9 is formed by applying a material 11 on a section of the catheter shaft portion 2 between the distal end 8 of the balloon and the front end 10 of the catheter shaft portion 2. The material 11 is a more flexible one than the material of the catheter shaft portion 2 and the catheter tip portion 7. This material 11 can be for example applied at the desired position in the form of a ring or band member. In the especially advantageous embodiment shown in FIG. 2, a pre-fixing of the ring material 11 is carried out by applying a shrinking foil 12. Subsequently, radiation energy, indicated in FIG. 2 by the two waved arrows L, is applied to the material 11, such that the integration of the material 11 into the material of the catheter shaft portion 7 as shown in FIG. 1. This results in reduction of the original material of the catheter shaft portion 7 in the section forming the joint portion 9. Thus, the more flexible material now surrounds this reduced section such that the formation of the flexible joint portion 9 is achieved. Preferably, the diameter of the joint portion 9 is the same as the diameter of the original material of the catheter shaft portion 7 in the section that forms the joint portion 9.

In FIG. 3, a second embodiment of an inventive catheter 1 is disclosed, the catheter 1 again comprising a catheter shaft portion 2 having a catheter tip portion 7 with a distal front end 10. However, the catheter 1 shown in FIG. 3 does not comprise a balloon. Accordingly, the joint portion 9, which corresponds in principle to those of FIGS. 1 and 2, is arranged proximal to the catheter tip portion 7.

The catheter tip portion 7 can again be made of the same material as the catheter shaft portion 2 or of a more rigid material.

In a further alternative embodiment, an ultrasonic head 13 shown in FIG. 3 can be provided at the distal end of the catheter shaft 2. In such an embodiment, the joint portion 9 is disposed between the ultrasonic head 13 and the distal end 10 of the catheter tip portion 7.

As used herein, the following directional terms "forward, rearward, above, downward, vertical, horizontal, below and transverse" as well as any other similar directional terms refer to those directions of a catheter configured according to the present invention. Accordingly, these terms, as utilized to describe the present invention should be interpreted relative to a vehicle equipped with the present invention.

The terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

The present application claims priority to prior European Patent Application No. 02029115.9. The entire disclosure of European Patent Application No. 02029115.9 is hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents. Thus, the scope of the invention is not limited to the disclosed embodiments.

What is claimed is:

1. A catheter comprising:
   a catheter shaft portion having a proximal end and a distal end, the catheter shaft portion being made of a first material and having a first diameter;
   a balloon having a proximal end and a distal end, the balloon being arranged at the distal end of the catheter shaft portion;
   a joint portion being more flexible than the catheter shaft portion and extending distally from the distal end of the catheter shaft portion, the joint portion including a portion of the catheter shaft portion and an overlying member disposed over the portion of the catheter shaft portion, the overlying member including a second material which is more flexible than the first material of the catheter shaft portion, the joint portion being disposed distal of the balloon and having a second diameter substantially equal to the first diameter; and
   a catheter tip portion disposed on an opposite side of the joint portion from the catheter shaft portion and extending distally from the joint portion;
   wherein the catheter tip portion is made of a material having a flexibility equal to or lower than the first material.

2. The catheter according to claim 1, wherein the catheter tip portion includes the first material of the catheter shaft portion.

3. The catheter according to claim 2, wherein the joint portion further includes the first material.

4. The catheter according to claim 3, wherein the catheter tip portion includes an additional material that stiffens the catheter tip portion relative to the distal end of the catheter shaft portion.

5. The catheter according to claim 3, wherein the catheter tip portion, at least some of the joint portion, and the catheter shaft portion are formed together as a one-piece, unitary member.

6. The catheter according to claim 5, wherein the second material of the joint portion is formed as a ring.

7. The catheter according to claim 1, wherein the catheter tip portion includes an additional material that stiffens the catheter tip portion relative to the distal end of the catheter shaft portion.

8. The catheter according to claim 1, wherein the catheter tip portion is more rigid than the distal end of the catheter shaft portion.

9. The catheter according to claim 8, wherein the catheter tip portion includes the first material of the catheter shaft portion.

10. The catheter according to claim 9, wherein the catheter tip portion includes an additional material that stiffens the catheter tip portion relative to the distal end of the catheter shaft portion.

11. The catheter according to claim 9, wherein the second material of the joint portion is formed as a ring.

12. The catheter according to claim 1, wherein the joint portion is integrated into the catheter tip portion.

13. The catheter according to claim 1, wherein the second material of the joint portion is formed as a ring.

14. The catheter according to claim 13, wherein the second material of the joint portion is formed as a ring provided into a peripheral cavity of the joint portion, and wherein the diameter of the joint portion is essentially equal to the diameter of the distal end of the catheter shaft portion.

15. The catheter according to claim 1, wherein the second material of the joint portion is a plastic material.

* * * * *